United States Patent [19]

Tokashiki et al.

[11] Patent Number: 5,696,063
[45] Date of Patent: Dec. 9, 1997

[54] BASIC METAL SALT OF DITHIOCARBAMIC ACID AND LUBRICATING OIL COMPOSITION CONTAINING SAID SALT

[75] Inventors: Michihide Tokashiki, Kawagoe; Hirotaka Tomizawa, Tokorozawa; Katsuya Arai, Iruma-gun, all of Japan

[73] Assignee: Exxon Chemical Patents Inc., Linden, N.J.

[21] Appl. No.: 666,461

[22] PCT Filed: Dec. 28, 1994

[86] PCT No.: PCT/JP94/02290

§ 371 Date: Sep. 11, 1996

§ 102(e) Date: Sep. 11, 1996

[87] PCT Pub. No.: WO95/18100

PCT Pub. Date: Jul. 6, 1995

[30] Foreign Application Priority Data

Dec. 30, 1993 [JP] Japan ................. 5-354602

[51] Int. Cl.$^6$ ................................ C10M 135/18
[52] U.S. Cl. ............... 508/363; 508/364; 508/365; 556/38
[58] Field of Search ...................... 508/363, 364, 508/365; 556/38

[56] References Cited

U.S. PATENT DOCUMENTS

| | | | |
|---|---|---|---|
| 3,297,733 | 1/1967 | Kornicker | 556/38 |
| 4,203,999 | 5/1980 | Martin et al. | 556/38 |
| 4,681,957 | 7/1987 | Singhal et al. | 556/38 |
| 4,859,787 | 8/1989 | Spiess et al. | 558/235 |
| 5,364,952 | 11/1994 | Spiess et al. | 508/363 |

*Primary Examiner*—Jacqueline V. Howard
*Attorney, Agent, or Firm*—Harvey L. Cohen

[57] ABSTRACT

The present invention provides novel basic metallic salts of dithiocarbamic acid, in which the content of the basic ingredient (=a×3×100) is 30–100 mol %, represented by general formula (1):

$$\left[ \begin{matrix} R^1 \\ R^2 \end{matrix} \!\!\!\diagdown\!\! N-\underset{\underset{S}{\|}}{C}-S-M-S-\underset{\underset{S}{\|}}{C}-N \!\!\diagup\!\! \begin{matrix} R^3 \\ R^4 \end{matrix} \right] \cdot aZnO \quad (1)$$

wherein $R^1$ to $R^4$, which may be the same or different, are each a lipophilic group having 1–30 carbon atoms, M is a metal atom selected from the group consisting of zinc, copper, nickel, iron, cadmium, silver, lead, antimony, tin, and bismuth, and "a" is a coefficient of $1/3$ to $1/10$, said basic metallic salts of dithiocarbamic acid containing no phosphorus atoms and imparting low-wear properties when used as an additive for lubricating oils. The present invention also provides lubricating oil compositions containing in a lubricating base oil said basic metal salt of dithiocarbamic acid, which compositions are excellent in wear-resistant properties and frictional characteristics and suitable as a lubricating oil for automotive internal combustion engines.

6 Claims, No Drawings

BASIC METAL SALT OF DITHIOCARBAMIC ACID AND LUBRICATING OIL COMPOSITION CONTAINING SAID SALT

FIELD OF THE INVENTION

The present invention relates to a basic metal salt of dithiocarbamic acid and a lubricating oil composition containing said salt. A lubricating oil composition excellent in wear-resistant properties and friction-decreasing properties is obtained by adding a basic metal salt of dithiocarbamic acid to a lubricating base oil, specifically, to a hydrocarbon oil. The lubricating oil composition of the present invention is especially suitable as a lubricating oil for automotive internal combustion engines (an engine oil).

BACKGROUND OF THE INVENTION

Recently, as internal combustion engines such as automotive engines have gotten higher power, engine parts such as valve gear systems and cylinders have been placed under such severe conditions that they are exposed to high temperatures, and the frequency of contact per unit time between metals is increased. Under such severe conditions, the wear-inhibiting properties of an engine oil for engine parts such as these valve gear systems and cylinders have been regarded as being important.

To improve engine oil performance various kinds of additives have been compounded. For example, zinc dithiophosphate shows an excellent wear-inhibiting performance besides acting as an anti-oxidant and a corrosion inhibitor. From the aspect of both its multifunctionality and effect it is widely used in engine oils or in a hydraulic actuation oil. To improve the wear-inhibiting properties of engine oils an increase in an added amount of the zinc dithiophosphate has been conceived; however, since the phosphorus (P) in it poisons any exhaust emission purification catalyst and any oxygen sensor to significantly decrease the performance of an exhaust gas emission-control system, the added amount must be limited.

Thus the development of an additive for lubricating oils has been expected, said additive containing no phosphorus and having excellent friction-inhibiting properties; however, it has been difficult to find an additive showing a sufficient performance.

SUMMARY OF THE INVENTION

1. Disclosure of the Invention

One object of the present invention resides in providing a novel compound that can impart excellent wear-resistant properties to a lubricating oil when the compound is used as an oil additive for a lubricating oil.

Another object of the present invention resides in providing a lubricating oil composition excellent in wear-resistant properties and frictional characteristics and that is especially suitable for a lubricating oil for automotive internal combustion engines.

2. Means to Resolve the Problems

As a result of the extensive study by the inventors of the present invention to develop a lubricating oil containing no, or a very low content of, phosphorus, and having excellent wear-resistant properties, they found that when a basic metallic salt of dithiocarbamic acid was synthesized and its performance as an additive for lubricating oils was evaluated, a lubricating oil composition showing excellent wear-resistant properties and good frictional characteristics resulted, as compared with the case where a general-purpose zinc dithiophosphate or its corresponding neutral metallic salt of dithiocarbamic acid was added.

Among basic metallic salts of dithiocarbamic acid, those in which the average number of the carbon atoms of each of the lipophilic groups, such as an alkyl group, is more than 8, are excellent in solubility in base oils. The use of such a basic metallic salt of dithiocarbamic acid with an oil-soluble amine compound allows a further improvement in wear-resistant properties. The use of such a basic metallic salt of dithiocarbamic acid with a friction-decreasing agent results in a better effect in decreasing the coefficient of friction.

Wear-resistant properties of zinc dithiophosphate may be lost by a mutual action with another additive that may exist with it. For example, it was known that the wear-resistant properties were decreased by the coexistence with an oil-soluble amine compound such as succinic imide or an alkyl amine. Thus the excellent wear-resistant properties of a basic metallic salt of dithiocarbamic acid shown in the presence of an oil-soluble amine compound are very unique.

According to the present invention a lubricating oil composition containing no, or a very low content of, phosphorus, and excellent in wear-resistant properties and frictional characteristics, can be obtained without the use of a phosphorus-containing compound as an additive or by limiting the amount of any phosphorus-containing compound used to a small amount.

Based on this knowledge the present invention has been completed.

Thus according to the present invention a basic metallic salt of dithiocarbamic acid is represented by general formula (1):

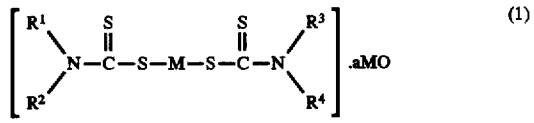

wherein $R^1$ to $R^4$, which may be the same or different, are each an oil-soluble group having 1–30 carbon atoms, M is a metal atom selected from the group consisting of zinc, copper, nickel, iron, cadmium, silver, lead, antimony, tin, and bismuth, and "a" is a coefficient in the range of ⅓ to ¹⁄₁₀, in which the content ratio of the basic ingredient is 30–100 mol %.

DETAILED DESCRIPTION OF THE EMBODIMENT

The present invention will be stated in detail below.

(Basic salt of dithiocarbamic acid)

The basic metallic salt of dithiocarbamic acid used in the present invention is a different compound from a neutral metallic salt of dithiocarbamic acid.

Generally a metallic salt of dithiocarbamic acid (below represented by MDDC) is designated by a compound represented by the following general formula (2):

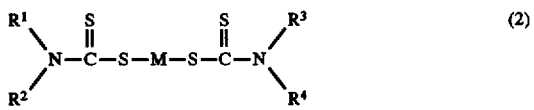

wherein $R^1$ to $R^4$ are each a lipophilic group such as an alkyl group, aryl group, alkylaryl group, and arylalkyl group, and M is a metal atom selected from the group consisting of zinc, copper, nickel, iron, cadmium, silver, lead, antimony, tin, and bismuth. Among the MDDCs, zinc dithiocarbamate (below represented by ZDDC), wherein the metal atom (M) is zinc (Zn), is a representative one.

When each of $R^1$ to $R^4$ is represented by R, MDDC is represented by $M(R_2NCS_2)_2$. When $R_2NCS_2$ is represented by DTC, MDDC is represented by $M(DTC)_2$. The $M(DTC)_2$ shows weak acidity, and is generally called a neutral metal salt of dithiocarbamic acid (neutral salt) (below represented by N-MDDC).

On the other hand, a basic salt of MDDC (below referred to as a basic ingredient, or B-MDDC) is produced upon the synthesis of MDDC when an excess amount of a metal ion is present in a basic reaction system. The basic salt in which the basic ingredients are 100 mol % is a complex formed from 3 mol $M(DTC)_2$ and 1 mol MO, and is a compound represented by general formula (3):

$$[M(DTC)_2]_3 \cdot MO \qquad (3)$$

This compound can be represented based on the composition ratio of M, DTC, and O, by the following general formulas (4), (5), and (6):

| | |
|---|---|
| $M(DTC)_2 \cdot 1/3MO$ | (4) |
| $(DTC)_6M_4O$ | (5) |
| $(DTC)_3M_2OH$ | (6) |

In the present invention a metallic salt of dithiocarbamic acid containing a basic ingredient in the ratio of 30–100% is used as the basic metallic salt of dithiocarbamic acid.

The content (mol %) of any basic ingredient in MDDC represents the value determined according to the following method of measurement. That is, when a sample MDDC is shown as $M(DTC)_2 \cdot aMO$ and the coefficient "a" is determined, the content of the basic ingredient can be calculated.

To calculate the value of the coefficient "a," the sample MDDC is first dissolved in isopropyl alcohol containing 10% by weight of water. Then the N-MDDC ingredient is titrated with 1/10N of NaOH using a phenolphthalein indicator (Titration I). In contrast, the MO ingredient is titrated with 1/10N HCl using a thymol blue indicator (Titration II). Each reaction formula in these titrations is represented by the following:

Titration I:

$$M(DTC)_2 \cdot aMO + 2NaOH \rightarrow 2NaDTC + M(OH)_2 + aMO \qquad (7)$$

Titration II:

$$M(DTC)_2 \cdot aMO + 2aHCl \rightarrow M(DTC)_2 + aMCl_2 + aH_2O \qquad (8)$$

From the result of the measurement, coefficient "a" is calculated by following formula (9):

$$a = \frac{MO(g\text{-mol/g})}{M(DTC)_2(g\text{-mol/g})} \qquad (9)$$

The content of the basic ingredient (mol %) is calculated by the following formula (10):

Content of Basic Ingredient=a×3×100 (mol %)    (10)

When the coefficient "a" is 1/3, the metallic salt of dithiocarbamic acid is a compound of the composition represented by any of general formulas (3) to (6), and the content of the basic ingredient is 100 mol %.

Although in the present invention an MDDC in which the content of the basic ingredient is 30–100 mol % (below referred to as a basic MDDC) may be used, the content is preferably 50–100 mol %, and more preferably 70–100 mol %. An MDDC in which the content of the basic ingredient is less than 30 mol % shows less effect in improving wear-resistant properties and frictional characteristics for lubricating base oils.

The four lipophilic groups $R^1$ to $R^4$ may be the same or different, and are preferably each an alkyl group having 1–30 carbon atoms, an aryl group having 6–30 carbon atoms, an alkylaryl group having 7–30 carbon atoms, or an arylalkyl group having 7–30 carbon atoms. A basic MDDC in which the average number of carbon atoms of each of $R^1$ to $R^4$ is 8 or less is insoluble, or slightly soluble, in a lubricating base oil. It is desired that after a basic MDDC having lipophilic groups of such short chains is in advance reacted with an oil-soluble amine compound to form a complex, which increases the solubility in a base oil, the complex is added to the base oil.

An additive for a lubricating oil must be, besides improving the performance of the lubricating oil, easily solubilized in a lubricating base oil to form a uniform composition. From this aspect, as the additive a basic MDDC having $R^1$ to $R^4$ of such a long-chain that the average number of the carbon atoms of each of $R^1$ to $R^4$ is more than 8 is preferred, since the solubility of the basic MDDC in a base oil is high. When each number of the carbon atoms exceeds 30, although the solubility in a lubricating oil is improved, the wear-resistant properties decrease. Each of these lipophilic groups preferably has 10–25 carbon atoms. A basic ZDDC may be used alone, or two or more basic ZDDCs may be used together.

A neutral or basic MDDC can be obtained by reacting an alkaline metal salt of DTC such as potassium dialkyldithiocarbamic acid with a metal nitrate such as zinc nitrate in the presence of a base such as sodium hydroxide. By adjusting the amount of the metal ions present in a reaction system the content of the basic ingredient can be adjusted.

(Lubricating Oil Composition)

According to the present invention a lubricating oil composition is obtained by adding said basic metal salt of dithicarbamic acid to a lubricating base oil.

Lubricating Base Oil

The lubricating base oils used in the present invention are not specifically limited, and conventionally known and various mineral oils or synthetic lubricating oils can be used. As the mineral oils, a raffinate obtained by solvent-refining a lubricating oil material with an aromatic extraction solvent such as phenol or furfural, a hydrogenation-treated oil obtained by a hydrogenation treatment with a hydrogenation-treating catalyst such as cobalt or molybdenum supported on silica-alumina as a carrier, a mineral oil such as a lubricating oil distillate obtained by the isomerization of wax, as, for example, 60 Neutral Oil, 100 Neutral Oil, 150 Neutral Oil, 300 Neutral Oil, 500 Neutral Oil, and Bright Stock, are exemplified. As the synthetic lubricating oils, poly-α-olefins, polybutene, alkylbenzenes, polyol esters, and dibasic acid esters, are exemplified. Such a base oil can be used alone, or two or more such base oils can be mixed and used.

Basic Metal Salt of Dithiocarbamic Acid

According to the present invention a lubricating oil composition excellent in wear-resistant properties and good in frictional characteristics is obtained by using as an additive for the lubricating oil said basic metal salt of dithiocarbamic acid (basic MDDC).

The compounding ratio of the basic MDDC is usually based on the total amount of the composition being 0.05–1.5% by weight, preferably 0.1–1.2% by weight, more preferably 0.2–1.0% by weight. When the compounding ratio of the basic MDDC is too low the effects of the wear-resistant properties and friction-decreasing properties are insufficient, and even if the amount is very high the improving effects do not increase above a certain degree.

Among basic MDDCs, a basic zinc dithiocarbamate (basic ZDDC) in which, as the metal salt, zinc is used, is preferred. For the solubility for lubricating base oils, a basic MDDC in which the average number of the carbon atoms of each lipophilic group is more than 8 is preferred, and a basic MDDC in which the carbon numbers of each lipophilic group is 10–25 is more preferred. Much more preferred is a basic MDDC in which each lipophilic group is an alkyl group having 10–25 carbon atoms.

Oil-soluble Amine Compound

When a basic MDDC of the present invention is used with an oil-soluble amine compound, improved wear-resistant properties and frictional characteristics result. Also, when a basic MDDC is slightly soluble in a lubricating base oil, it is preferred in advance to form a complex of the basic MDDC and an oil-soluble amine compound, and then the complex is added to a base oil, since the complex is easily solubilized to form a uniform lubricating oil composition.

As the oil-soluble amine compounds used in the present invention, ash-free detergent dispersants such as polyalkenyl succinic imides, polyalkenyl succinic amides, and alkylbenzyl amines, alkylamines such as oleylamine and 2-ethylhexylamine, alkyldiamines, and alkylpolyamines, are exemplified.

As the polyalkenyl succinic imide-based ash-free detergent dispersants, a product obtained by reacting a polybutenyl succinic anhydride with a polyamine such as a polyethylene polyamine is exemplified.

The compounding ratio of the oil-soluble amine compound is typically 0.1–10.0% by weight, preferably 0.2–8.0% by weight, and more preferably 0.3–5.0% by weight. If the compounding ratio of the oil-soluble amine compound is too low, the effect of its combination with a basic MDDC becomes insufficient, and if the ratio is too high the wear-resistant properties often decrease rather than increase.

To in advance form a complex of a basic MDDC and an oil-soluble amine compound, a preferable process is, for example, to heat a lubricating base oil containing the basic MDDC and the oil-soluble amine in relatively high concentrations. For example, when a base oil containing a basic MDDC in an amount of 1.5–7% by weight and an oil-soluble amine compound in 1.5–25% by weight is stirred, usually at 40°–220° C., preferably at 120°–200° C., usually for 1–60 minutes, preferably 1–30 minutes, the basic MDDC and the oil-soluble amine compound form a complex, which is uniformly solubilized in the base oil. If the resulting relatively high concentration of a complex solution is diluted with a lubricating base oil, a uniform lubricating oil composition containing both compounds in a given ratio is readily obtained.

Friction-decreasing Agent

If a basic MDDC of the present invention is used with a friction-decreasing agent, the effect in decreasing the coefficient of friction significantly increases.

As the friction-decreasing agents, amines, phosphoric esters, organic molybdenum compounds, higher alcohol esters, etc. are exemplified. Those are usually used in a ratio of 0.05–5.0% by weight. Among the above friction-decreasing agents, especially preferred are sulfurized molybdenum dialkyldithiocarbamates represented by general formula (11) and sulfurized molybdenum dialkyldithiophosphates represented by general formula (12):

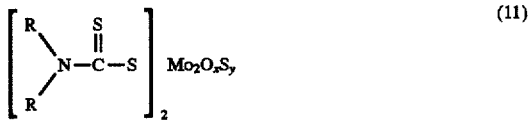

For R in formulas (11) and (12), alkyl groups and alkenyl groups having 8–18 carbon atoms are exemplified, such as 2-ethylhexyl, n-octyl, nonyl, decyl, tridecyl, and oleyl. In the formulas, x+y=4.

Other Additives

To a lubricating oil composition of the present invention, besides the above additives, if required another wear-resistant agent, an ash-free detergent dispersant, an anti-oxidant, a metal detergent, a viscosity index-improving agent, a pour-point lowering agent, a rust-preventive agent, a defoaming agent, a corrosion-preventive agent, etc. may be properly added.

As ash-free dispersants, succinic imides, succinic amides, benzyl amines, and esters, are exemplified. They may be typically used in a ratio of 0.5–7.0% by weight.

As wear-resistant agents, metal salts of dithiophosphoric acid (the metal may be Zn, Pb, Sb, etc.), neutral metal salts of dithiocarbamic acid (the metal may be Zn, etc.), sulfur compounds, phosphate esters, phosphite esters, etc., are exemplified. They are usually used in a ratio of 0.05–5.0% by weight.

As the anti-oxidant agents, amine-based anti-oxidant agents such as alkylated dipheylamines, phenyl-α-naphtyl amine, and alkylphenyl-α-naphtyl amines, and phenolic anti-oxidant agents such as 2,6-di-t-butylphenol and 4,4'-methylene-bis(2,6-di-tert-butylphenol), are exemplified. They are used in a ratio of 0.05–2.0% by weight.

As the metal detergents, neutral and perbasic salts of an alkaline earth metal, for example, Ca-sulfonate, Mg-sulfonate, Ba-sulfonate, Ca-phenate, and Ba-phenate, are exemplified. They are usually used in a ratio of 0.1–5.0% by weight.

As the viscosity-index improving agents, polyalkylmethacrylates, polyisobutyrenes, ethylene-propylene copolymers, and hydrogenated styrene-butadiene copolymers, are exemplified. They are usually used in a ratio of 1–35% by weight.

As rust-preventive agents, alkenyl succinic acids or partially esterified alkenyl succinic acids, are exemplified.

As defoaming agents, dimethyl polysiloxane and polyacrylate are exemplified.

The lubricating oil compositions of the present invention show superior wear-resistant properties and comparative oxidation stability over a general-purpose dithiophosphoric acid ester and a neutral MDDC, and good frictional characteristics. The lubricating oil composition of the present invention significantly decreases the coefficient of friction by adding to the composition a friction-decreasing agent such as molybdenum sulfide dialkyl dithiophosphate.

The lubricating oil compositions of the present invention are for use for any lubricating oil in which wear-resistant properties and low frictional characteristics are required, such as automotive engine oils, gear oils, trans-axle oils, hydraulic fluids, spindle oils, and machine oils.

EXAMPLES

The present invention is especially illustrated by the following synthetic examples of basic ZDDCs and neutral ZDDCs and Examples, but is not limited to them.

Synthetic Example 1 (A Synthetic Example of a Basic ZDDC)

246.62 g (0.5281 g-mol) of a potassium salt of dinormal lauryl dithiocarbamic acid and 7.04 g (0.1760 g-mol) of NaOH were fed to a reactor, to which water was added, to be dissolved. Then an aqueous solution containing 104.71 g (0.3520 g-mol) of $Zn(NO_3)_2 \cdot 6H_2O$ was added to the reactor. The resulting white solid precipitate was filtered and the white solids were subjected to suction drying by a pump. The thus-obtained white solids were washed with ether. The ether solution was removed, and to it petroleum ether was added, and the solution was allowed to stand in a refrigerator to obtain a starch syrup-state substance of a basic zinc salt of dinormal lauryl dithiocarbamic acid (the basic ingredient was 100 mol %; B-n-$C_{12}$ ZDDC).

Synthetic Example 2 (Synthetic Example of a Basic ZDDC)

This Example was conducted similarly to Synthetic example 1, except that instead of using a potassium salt of dinormal lauryl dithiocarbamic acid, a potassium salt of dinormal oleyl dithiocarbamic acid was used to obtain a basic zinc salt of dinormal oleyl dithiocarbamic acid (the basic ingredient was 100 mol %; B-n-$C_{18}$ ZDDC).

Synthetic Example 3 (a Synthetic Example of a Neutral ZDDC)

246.62 g of a potassium salt of dinormal lauryl dithiocarbamic acid (0.5281 g-mol) and 7.04 g of NaOH (0.1760 g-mol) were fed to a reactor, to which water was added to be dissolved. Then an aqueous solution containing 78.53 g (0.2640 g-mol) of $Zn(NO_3)_2 \cdot 6H_2O$ was added to the reactor. Except for the above, a starch syrup-state substance of a zinc salt of dinormal lauryl dithiocarbamic acid (the basic ingredient was 0 mol %; N-n-$C_{12}$ZDDC) was obtained similarly to Synthetic example 1.

Synthetic Example 4 (Synthetic Example of a Neutral ZDDC)

This example was conducted similarly to Synthetic example 3, except that instead of using a potassium salt of dinormal lauryl dithiocarbamic acid, a potassium salt of a dinormal oleyl dithiocarbamic acid was used to obtain a zinc salt of a dinormal oleyl dithiocarbamic acid (the basic ingredient was 0 mol %; N-n-$C_{18}$ ZDDC).

Synthetic Example 5 (Synthetic Example of a Basic ZDDC)

This example was conducted similarly to Synthetic example 1, except that the added amount of $Zn(NO_3)_2 \cdot 6H_2O$ was adjusted to obtain a basic zinc salt of a dinormal lauryl dithiocarbamic acid in which the basic ingredient was 25 mol % (the basic ingredient was 25 mol %; B-n-$C_{12}$ZDDC).

Synthetic Example 6 (Synthetic Example of a Basic ZDDC)

This Example was conducted similarly to Synthetic example 1, except that the added amount of $Zn(NO_3)_2 \cdot 6H_2O$ was adjusted to obtain a basic zinc salt of a dinormal lauryl dithiocarbamic acid in which the basic ingredient was 32 mol % (the basic component was 32 mol %; B-n-$C_{12}$ZDDC).

Example 1 (Solubility Test of Basic ZDDCs and Neutral ZDDCs)

Basic ZDDCs or neutral ZDDCs in which the number of the carbon atoms of the lipophilic groups is 12 or 18, as shown in Table 1 (those were synthesized in the above Synthetic examples), were added to a mineral oil (a solvent-refined 100-SN mineral oil) in the ratio shown in Table 1.

Solubility Tests

After preparing a lubricating oil composition by adding a basic ZDDC or a neutral ZDDC to a base oil the solubilities of the basic ZDDCs and the neutral ZDDCs were visually observed and evaluated as the two following grades:

○: uniformly dissolved

×: Precipitate is observed.

The results are summarized in Table 1.

TABLE 1

| Experiment No. | Zinc Dithiocarbamate | | | | | Synthetic Example of Compound Used |
|---|---|---|---|---|---|---|
| | Lipophilic Group | Basic Ingredient Content (Mol %) | Added Amount (% by weight) | Solubility | Note | |
| 1 | $C_{12}$ | 0 | 0.1 | ○ | Comparative example | 3 |
| 2 | $C_{12}$ | 0 | 0.5 | ○ | Comparative example | 3 |
| 3 | $C_{12}$ | 100 | 0.1 | ○ | Example | 1 |
| 4 | $C_{12}$ | 100 | 0.5 | ○ | Example | 1 |
| 5 | $C_{18}$ | 0 | 0.1 | ○ | Comparative example | 4 |
| 6 | $C_{18}$ | 0 | 0.5 | ○ | Comparative example | 4 |
| 7 | $C_{18}$ | 100 | 0.1 | ○ | Example | 2 |
| 8 | $C_{18}$ | 100 | 0.5 | ○ | Example | 2 |
| 9 | $C_{12}$ | 25 | 0.5 | ○ | Comparative example | 5 |
| 10 | $C_{12}$ | 32 | 0.5 | ○ | Example | 6 |

As is clearly shown from the results in Table 1, any of the basic ZDDCs and neutral ZDDCs in which the number of the carbon atoms of the lipophilic groups is 12 or 18 shows good solubility in a base oil.

Example 2 (Shell Four-Ball Test)

To evaluate the effect for each wear-resistant property and the decrease in the coefficient of friction, Shell four-ball wear-resistance tests were conducted. For a comparison, commercially available zinc dithiocarbamate (ZDDP) (Paranox 15 produced by Exxon Chemical Company) and neutral ZDDCs were used.

The composition of the lubricating oil and the conditions in the tests were as follows:

(1) Base Oil

Mineral oil: solvent-refined 100-SN mineral oil (100 Neutral mineral oil)

(2) Zinc dithiocarbamate (the added amount is a value in relation to N-ZDDP)

① B-n-$C_{12}$ZDDC: basic zinc salt of dinormal lauryl dithicarbamic acid (basic ingredient is 100 mol %)

② B-n-$C_{12}$ZDDC: basic zinc salt of dinormal lauryl dithicarbamic acid (basic ingredient is 32 mol %)

③ B-n-$C_{12}$ZDDC: basic zinc salt of dinormal lauryl dithicarbamic acid (basic ingredient is 25 mol %)

④ N-n-$C_{12}$ZDDC: neutral zinc salt of dinormal lauryl dithicarbamic acid (basic ingredient is 0 mol %)

⑤ B-n-$C_{18}$ZDDC: basic zinc salt of dinormal oleyl dithicarbamic acid (basic ingredient is 100 mol %)

⑥ N-n-$C_{18}$ZDDC: neutral zinc salt of dinormal oleyl dithicarbamic acid (basic ingredient is 0 mol %)

(3) Oil-soluble Amine Compound succinic imide: a commercially available polybutenyl succinic imide-type detergent dispersant (ECA4360, produced by Exxon Chemical Company)

Other ingredients are as shown in Table 2.

Wear-resistance Test

The conditions in the Shell four-ball tests were as follows: the load was 40 kg; the oil temperature was 90° C.; the number of revolutions was 3,600 rpm; the test time was 30 minutes.

The results are shown in Table 2.

better wear-resistant properties and an effect in decreasing the coefficient of friction compared with those of the corresponding neutral ZDDCs. Further, any lubricating oil composition of the present invention shows an even better coefficient of friction by adding to the composition molybdenum sulfide dithiocarbamate, which is a friction-decreasing agent. According to the present invention, a basic metal salt of dithiocarbamic acid that is a novel compound is provided. Also, by the present invention, a lubricating oil composition that is good in wear-resistant properties, frictional characteristics, and oxidation stability properties, is provided. Any lubricating oil composition of the present invention shows better wear-resistant properties compared with those of a lubricating oil composition in which a conventional zinc dithiophosphate or a neutral zinc dithiocarbamate is added, and has an effect in decreasing the coefficient of friction (frictional characteristics). Also, any lubricating oil composition of the present invention can have no, or a very low, phosphorus content, and thus is especially suitable for a lubricating oil composition for internal combustion engines.

We claim:

1. A basic metal salt of dithiocarbamic acid in which the content of the basic ingredient (=a×3×100) is 30–100 mol % represented by general formula (1):

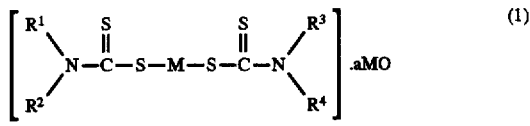

wherein $R^1$ to $R^4$, which may be the same or different, are each a lipophilic group having 1–30 carbon atoms, M is a metal atom selected from the group consisting of zinc, copper, nickel, iron, cadmium, silver, lead, antimony, tin, and bismuth, and "a" is a coefficient of $\frac{1}{3}$ to $\frac{1}{10}$.

2. The basic zinc salt of dithiocarbamic acid of claim 1 in which the lipophilic group having 1–30 carbon atoms is an

TABLE 2

| Experiment No. | Zinc Dithiocarbamate | | | Succinic Imide Dispersing Agent | Polymethacrylate Viscosity-Index Improver | Molibdenum Sulfide Dithiocarbamate Friction-decreasing Agent | Shell Four-ball Test | | Note |
|---|---|---|---|---|---|---|---|---|---|
| | Lipophilic Group | Basic ingredient Content (mol %) | Added Amount (% by weight) | Added Amount (% by weight) | Amount (% weight) | Added Amount (% by weight) | Ball Diameter After Wear(mm) | Coefficient of Friction | |
| 12 | $C_{12}$ | 0 | 0.5 | 6.0 | 4.0 | — | 0.44 | 0.096 | Comparative Example |
| 13 | $C_{12}$ | 100 | 0.5 | 6.0 | 4.0 | — | 0.40 | 0.087 | Example |
| 14 | $C_{12}$ | 100 | 0.5 | 6.0 | 4.0 | 0.5 | 0.51 | 0.063 | Example |
| 15 | $C_{18}$ | 0 | 0.5 | 6.0 | 4.0 | — | 0.45 | 0.091 | Comparative Example |
| 16 | $C_{18}$ | 100 | 0.5 | 6.0 | 4.0 | — | 0.39 | 0.085 | Example |
| 17 | $C_{18}$ | 100 | 0.5 | 6.0 | 4.0 | 0.5 | 0.49 | 0.058 | Example |
| 18 | $C_{12}$ | 25 | 0.5 | 6.0 | 4.0 | — | 0.44 | 0.095 | Comparative Example |
| 19 | $C_{12}$ | 32 | 0.5 | 6.0 | 4.0 | — | 0.41 | 0.088 | Example |
| 20 | $C_{12}$ | 32 | 0.5 | 6.0 | 4.0 | — | 0.48 | 0.065 | Example |
| 21 | Commercially Available ZDDP | — | 1.0 (*1) | 6.0 | 4.0 | — | 0.65 | 0.123 | Comparative Example |
| 22 | Commercially Available ZDDP | — | 1.0 (*1) | 6.0 | 4.0 | 0.5 | 0.63 | 0.065 | Comparative Example |

Note:

(*1) shows a product diluted in a diluting oil and containing an active ingredient in an amount of about 50% (primary $C_4/C_5$ alkyl group)

As is clear from the results of Table 2, any lubricating oil composition of the present invention shows better wear-resistant properties than any general-purpose zinc dithiophosphate (ZDDP), and has a good coefficient of friction, and has a sufficient performance as a lubricating oil composition having no, or a very low, phosphorus content. Also, the lubricating oil composition of the present invention has alkyl group having 1–30 carbon atoms, an aryl group having 6–30 carbon atoms, an alkylaryl group having 7–30 carbon atoms, or an arylalkyl group having 7–30 carbon atoms.

3. A lubricating oil composition containing in a lubricating base oil a basic metal salt of dithiocarbamic acid (A) in which the content of the basic ingredient (=a×3×100) is 30–100 mol % represented by general formula (1):

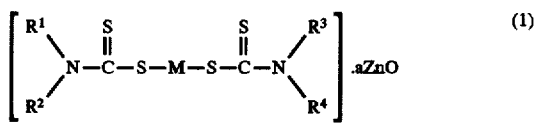

wherein $R^1$ to $R^4$, which may be the same or different, are each a lipophilic group having 1–30 carbon atoms, M is a metal atom selected from the group consisting of zinc, copper, nickel, iron, cadmium, silver, lead, antimony, tin, and bismuth, and "a" is a coefficient of ⅓ to ⅒.

4. The lubricating oil composition of claim 3 in which the basic metal salt of dithiocarbamic acid (A) is a compound in which the average number of carbon atoms of each of $R^1$, $R^2$, $R^3$, and $R^4$ in general formula (1) is more than 8.

5. The lubricating oil composition of claim 4, in which an oil-soluble amine compound (B) is further contained.

6. The lubricating oil composition of any of claims 3 to 5, in which at least one kind of friction-decreasing agent (C) selected from the group consisting of molybdenum sulfide dialkyldithiocarbamates and molybdenum sulfide dialkyldithiophosphates is contained.

* * * * *

UNITED STATES PATENT AND TRADEMARK OFFICE
CERTIFICATE OF CORRECTION

PATENT NO.  : 5,696,063
DATED       : Dec. 9, 1997
INVENTOR(S) : Michihide Tokashiki, et al It is certified that error appears in the above-identified patent and that said Letters Patent is hereby corrected as shown below:

In claim 3, column 11, Formula 1, change

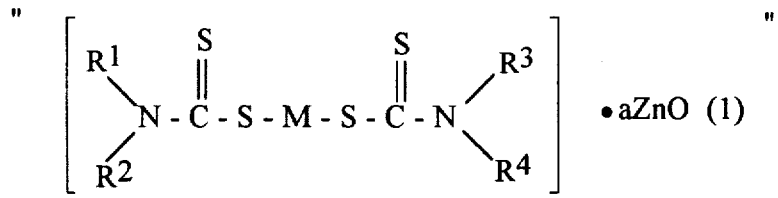

to

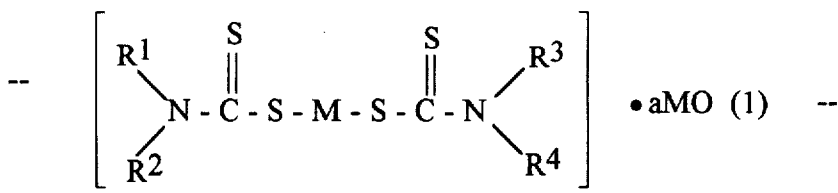

Signed and Sealed this

Twenty-fourth Day of February, 1998

Attest:

BRUCE LEHMAN

*Attesting Officer*       *Commissioner of Patents and Trademarks*